(12) United States Patent
Kamalakaran et al.

(10) Patent No.: US 10,342,454 B2
(45) Date of Patent: Jul. 9, 2019

(54) REAL-TIME MEDICAL DEVICE VISUALIZATION USING NANOMATERIALS

(75) Inventors: Sitharthan Kamalakaran, Pelham, NY (US); Balasundar Raju, Chester, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 883 days.

(21) Appl. No.: 14/112,664

(22) PCT Filed: Apr. 16, 2012

(86) PCT No.: PCT/IB2012/051877
§ 371 (c)(1),
(2), (4) Date: Oct. 18, 2013

(87) PCT Pub. No.: WO2012/143843
PCT Pub. Date: Oct. 26, 2012

(65) Prior Publication Data
US 2014/0046178 A1   Feb. 13, 2014

Related U.S. Application Data

(60) Provisional application No. 61/477,269, filed on Apr. 20, 2011.

(51) Int. Cl.
*A61B 5/06* (2006.01)
*A61B 17/00* (2006.01)
*A61B 34/20* (2016.01)
*A61B 90/00* (2016.01)

(52) U.S. Cl.
CPC ............. *A61B 5/061* (2013.01); *A61B 17/00* (2013.01); *A61B 34/20* (2016.02); *A61B 90/39* (2016.02); *A61B 2090/373* (2016.02); *A61B 2090/378* (2016.02); *A61B 2090/3735* (2016.02); *A61B 2090/397* (2016.02); *A61B 2090/3925* (2016.02); *A61B 2090/3933* (2016.02); *A61B 2090/3937* (2016.02); *A61B 2090/3941* (2016.02)

(58) Field of Classification Search
CPC ............ G01N 33/582; G01N 27/44726; A61B 19/44; A61B 19/54; A61B 2019/5441; A61B 2019/545; A61B 5/0059
USPC ................................. 600/407, 425, 473, 476
See application file for complete search history.

(56) References Cited

U.S. PATENT DOCUMENTS

| 5,921,933 A | 7/1999 | Sarkis et al. |
| 6,280,386 B1 * | 8/2001 | Alfano et al. ............... 600/431 |
| 9,192,685 B2 | 11/2015 | Allemann et al. |

(Continued)

FOREIGN PATENT DOCUMENTS

| CN | 101601607 A | 12/2009 |
| CN | 2009127142 A | 12/2009 |

(Continued)

*Primary Examiner* — Peter Luong

(57) ABSTRACT

A medical device and methods for locating the device include a structure having a length dimension and a surface (102). A volume (106) is associated with the surface and extends along a portion of the length dimension. Nanomaterials (108) are incorporated in the volume and configured to be responsive to an excitation signal such that the excitation signal generates a response from the nanomaterials to enable location of the structure within a subject.

10 Claims, 5 Drawing Sheets

(56) References Cited

U.S. PATENT DOCUMENTS

| | | | |
|---|---|---|---|
| 2003/0040685 A1* | 2/2003 | Lewkowicz et al. | 600/593 |
| 2006/0040388 A1* | 2/2006 | Bromberg | B01D 53/14 |
| | | | 435/375 |
| 2006/0173362 A1* | 8/2006 | Toms et al. | 600/478 |
| 2007/0100279 A1 | 5/2007 | Bates | |
| 2014/0046178 A1 | 2/2014 | Kamalakaran et al. | |

FOREIGN PATENT DOCUMENTS

| | | |
|---|---|---|
| RU | 2563369 A | 9/2015 |
| WO | WO2009021064 | 2/2009 |

\* cited by examiner

REAL-TIME MEDICAL DEVICE VISUALIZATION USING NANOMATERIALS

CROSS-REFERENCE TO PRIOR APPLICATIONS

This application is the U.S. National Phase application under 35 U.S.C. § 371 of International Application Serial No. PCT/IB2012/051877, filed on Apr. 16, 2012, which claims the benefit of U.S. Application Ser. No. 61/477,269, filed on Apr. 20, 2011. These applications are hereby incorporated by reference herein.

This disclosure relates to medical image visibility and more particularly to systems and methods for increasing device visibility in medical images.

Visualization of a catheter or a needle is important in many medical intervention procedures. The present standard for catheter visualization includes X-ray imaging with contrast dyes (fluoroscopy). Such procedures are invasive due to the ionizing radiation and toxicity of the dye itself. Conventional imaging techniques such as ultrasound or magnetic resonance imaging (MRI) are unable to provide clear contrast of catheter materials. Electromagnetic tracking sensors mounted on catheters for use in catheter visualization lack accuracy due to distortion of the electromagnetic field. In addition, accurate catheter visualization is challenging because, in general, catheters are characterized by uncontrollable angle dependent specular reflection.

In accordance with the present principles, a medical device and methods for locating the device include a structure having a length dimension and a surface. A volume is associated with the surface and extends along at least a portion of the length dimension. Nanomaterials are incorporated in the volume and configured to be responsive to at least one excitation signal such that the excitation signal generates a response from the nanomaterials to enable location of the structure within a subject.

A system for locating a medical device includes a medical device having nanomaterials incorporated therein, the nanomaterials being configured to be responsive to at least one excitation signal. An excitation source is configured to generate the at least one excitation signal to generate response emissions from the nanomaterials. A sensor is configured to receive the response emissions. An image processing module is configured to render the medical device in a medical image using the response emissions.

A method for locating a medical device includes providing a medical device having nanomaterials incorporated therein, the nanomaterials being configured to be responsive to at least one excitation signal; exciting the nanomaterials using the at least one excitation signal to generate response emissions from the nanomaterials; sensing the response emissions; and processing the response emissions to locate the medical device in relation to a medical image.

Another method for generating an image of a medical device includes exciting nanomaterials included in a medical device using a first electromagnetic frequency of excitation for the nanomaterials to obtain a first imagable response, the first imagable response being detectable over surrounding materials; exciting the nanomaterials included in the medical device using a second electromagnetic frequency of excitation for the nanomaterials to obtain a second imagable response which includes a realizable difference from the first imagable response, the second imagable response being detectable over the surrounding materials; and subtracting the first imagable response from the second imagable response to provide an image of the medical device relative to a subject.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
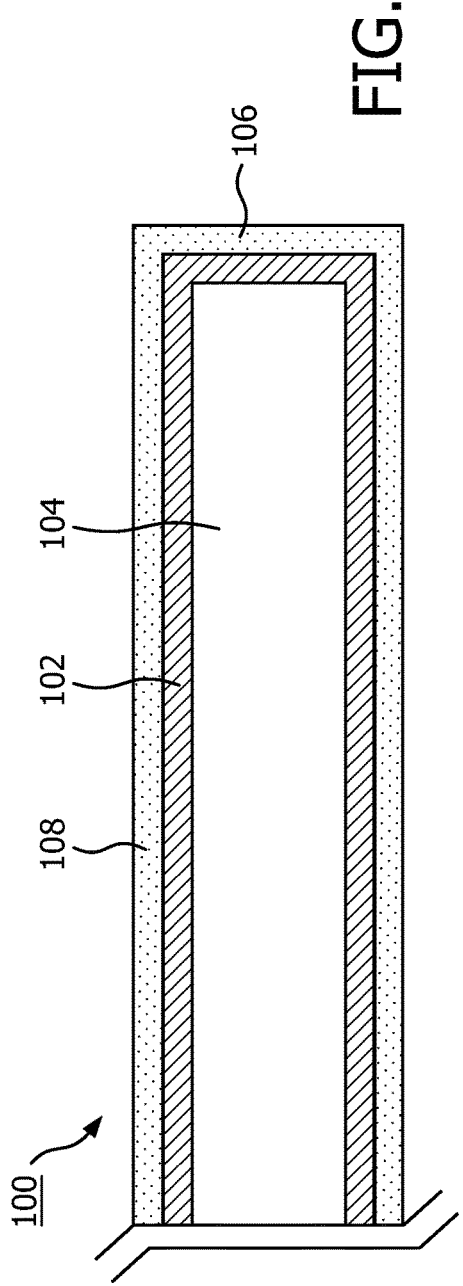
FIG. 1 is a partial cross-sectional view of a medical device having a solid layer or coating containing nanomaterials in accordance with one embodiment.

In accordance with the present principles, systems, devices and methods are provided which modify medical devices to have an additional layer of materials on or embedded within the device's surface. In one embodiment, nanomaterials are employed. The nanomaterials may be selected to have absorption properties for specific wavelengths. During a medical procedure or the like, an electromagnetic field is provided to a region of interest. Responsive to this field, the nanomaterials generate an acoustic signature from the impact of incident electromagnetic waves which is then detected using an acoustic detector.

In particularly useful embodiments, the nanomaterials that may be employed include, e.g., carbon nanotubes, nanorods or nanospheres. In other embodiments, an image subtraction method may be employed where electromagnetic radiation at two frequencies is used to better infer the location of the medical device inside of a patient.

It should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS., and in particular FIG. 4, may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a cross-sectional view of a portion of a medical device 100 is illustratively depicted in accordance with one embodiment. Device 100 may include, e.g., a catheter, a guide wire, an endoscope, a probe, a robot, an electrode, a filter device, a balloon device, a needle or other medical component, etc. Device 100 includes a device surface or wall 102 which may form a cavity 104. A material layer or volume 106 is formed on an outside of the device wall or surface 102. Layer 106 includes a composition to aid visualization of the medical device 100 in medical images.

In one embodiment, layer 106 includes a polymer material having suspended nanomaterials 108 in and/or on the layer 106. The polymer material may include a plastic, an epoxy, an adhesive, a resin, a paint, etc. Nanomaterial suspensions may be molded into or otherwise incorporated in a solid matrix and then formed into or deposited onto the surface of the device wall 102. The solid matrix with suspended nanoparticles can be manufactured with a PVA matrix, agarose gel, other polymer gels, or using silicone.

The nanomaterials 108 may include single-walled or multi-walled carbon nanotubes, metallic nanorods, nanospheres, nanocages, quantum dots that have optical properties dependant on incident wavelength or similar components. The nanomaterials 108 are selected to have specific absorption or scattering peaks at defined wavelengths. During a procedure, an electromagnetic field is provided to an area of interest. The nanomaterials 108 of layer 106 generate electromagnetic or acoustic signatures due to the interaction of the incident electromagnetic waves and the nanomaterials 108 that are different from the surrounding tissues inside a patient. A detection method can use photoacoustics, optical backscatter imaging, thermoacoustics either extracorporally or using an endoscope receiver, etc. An example of electromagnetic radiation that could be applied may include using an infra-red field of defined wavelength. In this example, a layer of gold nanorods with aspect ratios of 5.9 and an incident radiation having a wavelength at 1000 nm may be employed. In this way, the nanorods are excited and provide a visible and/or measurable response which can be employed to precisely locate the device 100 inside a patient.

Electromagnetic wave absorption spectra of the nanomaterials 108, such as, metallic nanospheres, nanorods, carbon nanotubes, etc. depend on the geometry of the materials. The behavior of quasiparticles, such as, excitons, phonons, and plasmons, and their interaction with incident waves greatly influences the absorption spectra as well. Other modifications such as doping or alloying of the nanomaterials 108 can also significantly influence their absorption spectra.

The physical origin of the absorption of electromagnetic waves by metallic nanoparticles, for example, is the coherent oscillation of the conduction band electrons induced by an electromagnetic field. These resonances are referred to as surface plasmons. Localized surface plasmon resonance depends on the physical dimensions of the particles, dielectric constant of the surrounding medium, and shape of the nanostructures.

Carbon nanotubes (CNTs) include a structure with carbon atoms arranged in a planar sheet called a graphene rolled into a tubular structure. CNTs can be classified as single-walled or multi-walled. Sizes of single walled CNTs may be about 1 nm in diameter and several hundreds of nanometers to micrometers in length. CNTs possess extraordinary electrical, thermal, and mechanical properties. The absorption of electromagnetic radiation by CNTs is governed by their geometry, in particular, their diameter and chirality (twist), as well as the dielectric properties of the surrounding medium.

Absorption spectra of CNTs are well described by their band gap properties. CNTs are direct band-gap materials, and their optical spectra have long been attributed to transitions between the energy states in the valence and conduction band leading to the usual van Hove resonances for the absorption spectra. However, other phenomena, in particular, the behavior of excitons (electron-hole pairs) in these quasi-one dimensional systems dominate significantly their optical absorption properties.

CNTs have well defined absorption peaks that correspond to the exciton state transitions. Additionally, doping can be used to significantly tune the resonance peaks of CNTs. The absorption properties of CNTs can be used advantageously for imaging. For example, CNTs absorb radiation at near infra-red wavelengths, at which inherent absorption by tissues is minimal. Thus, CNTs can be employed as effective photo-acoustic contrast agents.

For carbon nanotubes (CNT), the π plasmon resonance varies with nanotube diameter determined empirically as:

$$E_\pi = 4.8 + \frac{0.70}{d^2}$$

where $E_\pi$ is the energy and d is the nanotube diameter.

Another form of nanomaterials 108 includes nanospheres. Nanospheres may include, for example, gold. The absorption spectra of such materials also depend on the geometry such as the size and aspect ratio, and the behavior of plasmons (oscillations of the free electron gas density). Gold nanospheres with diameters of tens of nanometers exhibit an absorption peak at about 550 nm. With increasing size, the peak optical absorption shifts towards the red end of the visible spectrum.

For single element metallic nanospheres, a peak absorption wavelength of the metallic nanospheres is weakly dependent on the size with a general trend towards red shift with increasing size. For example, with gold nanospheres of size 22 and 99 nm, the peak absorption wavelengths are 520 nm and 575 nm, respectively.

Another stronger factor that determines the absorption peak of spherical nanoparticles is the addition of another metal to form an alloy. The peak absorption spectra of gold-silver alloy nanoparticles blue-shifts (decreases in wavelength) with decreasing gold mole fraction. For example, the peak spectra occurs at about 400 nm when the gold mole fraction is close to zero, increases to 450 nm for a mole fraction of 0.5 and further increases to 500 nm for a mole fraction of 0.80. Thus, nanopsheres can be tailored by their size and alloying to produce specific peak absorption spectra.

For alloyed nanospheres, alloy formation can be used to obtain a wider variety in the choice for a given peak wavelength. The following equation can be used to determine peak wavelength for an 18 nm gold-silver alloy nanosphere: $\lambda_{max}=130\chi_{Au}+390$ where $\lambda_{max}$ is the peak absorption wavelength in nm and $\chi_{Au}$ is the mole fraction of gold.

Another form of nanomaterials 108 includes nanorods. In contrast to nanospheres, the wavelength of peak absorption of, e.g., gold nanorods (i.e., cylindrical gold nanoparticles) depends only weakly on their diameter, instead increasing strongly with their aspect ratio. For example gold nanorods with mean aspect ratios of 5.9 and 3.7 exhibit peak optical absorptions at 1000 and 785 nm, respectively.

For example, for single element metallic nanorods, gold may be selected as an exemplary material due to its biological compatibility. The peak absorption wavelength of metallic nanorods may be given by the following equation: $\lambda_{max}=33.34\varepsilon_m R-46.31\varepsilon_m+472.31$ where $\lambda_{max}$ is the peak wavelength in nm, $\varepsilon_m$ is the dielectric constant of the surrounding medium, and R is the aspect ratio defined as the length of the rod divided by the width. Thus, the peak wavelength of absorption varies linearly with the aspect ratio as well as the medium's dielectric constant. A preferred peak wavelength may be chosen to be within the optical window of the human tissue in the infra-red region, e.g., 650 to 1200 nm. If the surrounding medium has a known dielectric constant (e.g., $\varepsilon_m=3$), this value can be inserted in the above equation to determine peak wavelength as a function of aspect ratio R. The medium's dielectric constant is a function of the aspect ratio and can be modeled as a monotonically decreasing function.

For alloyed nanorods, the optical properties vary as a function of the alloy composition and the length. There are multiple resonances including longitudinal and transverse modes. As an example, the transverse modes can be used for imaging since these peaks vary as a function of the alloy composition for a given length. The peak transverse mode wavelength (nm) varies as a function of the gold mole fraction $\chi_{Au}$: $\lambda_{max}=149\chi_{Au}+360$.

The longitudinal modes can also be used for differential imaging since these wavelengths vary as a function of rod length (or equivalently aspect ratios for a fixed size). For a 65% mold fraction of gold, the peak longitudinal wavelength red shifts from 716 nm for a length of 123 nm to 1467 nm for a length of 328 nm.

In addition to exhibiting spectral resonances, nanomaterials 108 have inherently different optical properties from biological tissues, which provide contrast mechanisms through imaging modalities such as optical coherence tomography. In such situations, the nanomaterials 108 are employed as scattering contrast agents.

Nanomaterials 108 provide a plurality of methods and materials to tune their electromagnetic wave absorption properties. These properties can be advantageously used in medical imaging applications to provide image contrast and opacity. For example, due to the low inherent absorption of most biological tissues in the near infra-red wavelengths, nanomaterials can provide optical contrast agents in, e.g., blood. Additionally, absorption properties of nanomaterials 108 also may lead to photoacoustic effects, which can be detected using imaging ultrasound scanners.

Figure 2:
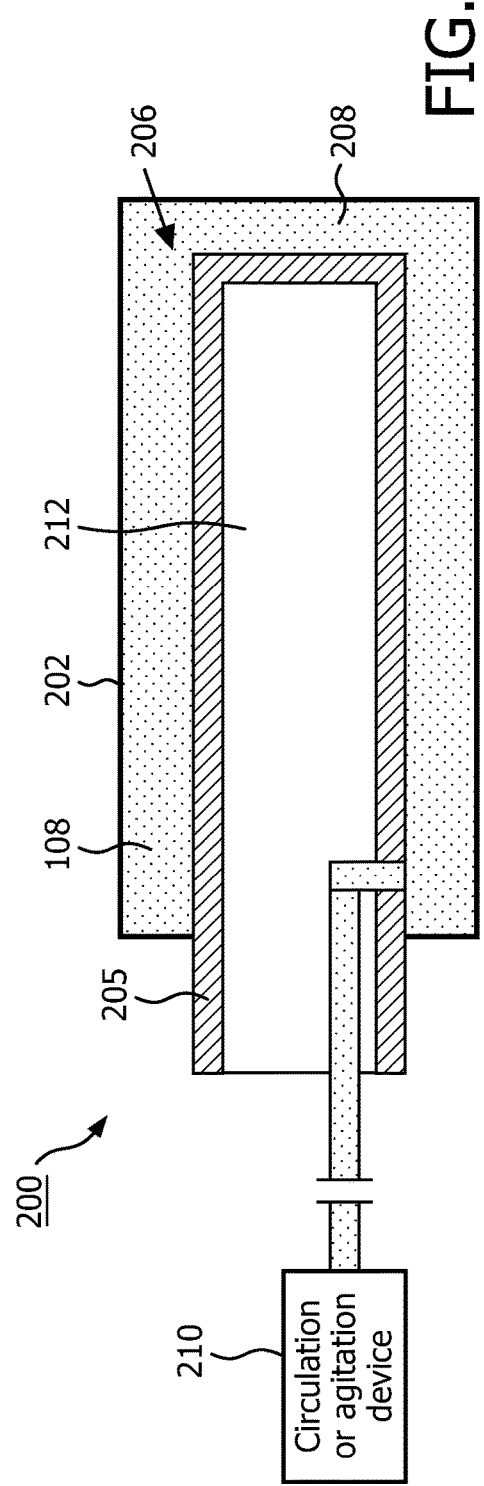
FIG. 2 is a partial cross-sectional view of a medical device having a tube forming an annular cavity containing nanomaterials in suspension in accordance with another embodiment.

Referring to FIG. 2, another medical device 200 is shown in accordance with another illustrative embodiment. Device 200 may take the same forms as device 100. Device 200 includes a concentric tube 202 that surrounds a portion or an entire device wall 205. The concentric tube 202 forms an annular cavity 206 between the device wall 205 and the tube 202. The annular cavity 206 is filled with nanomaterials 108 in a nanomaterial suspension 208. A fluid of the suspension 208 in the cavity 206 may include water, saline or other biocompatible materials. The nanomaterial suspension may be circulated to prevent settling of the nanomaterials 108 using a circulation/agitation device 210. The circulation/agitation device 210 may include one or more of an external pump, a vibration device, an electromagnetic stirring device which mixes by mixing ferromagnetic particles, etc. It should be understood that the circulation/agitation device 210 may be located at or on the device 200 or may be located externally to a patient during a procedure.

In another embodiment, an inner cavity 212 of the device 200 may be filled with the nanomaterial suspension 208 instead of or in addition to the annular cavity 206.

Figure 3:
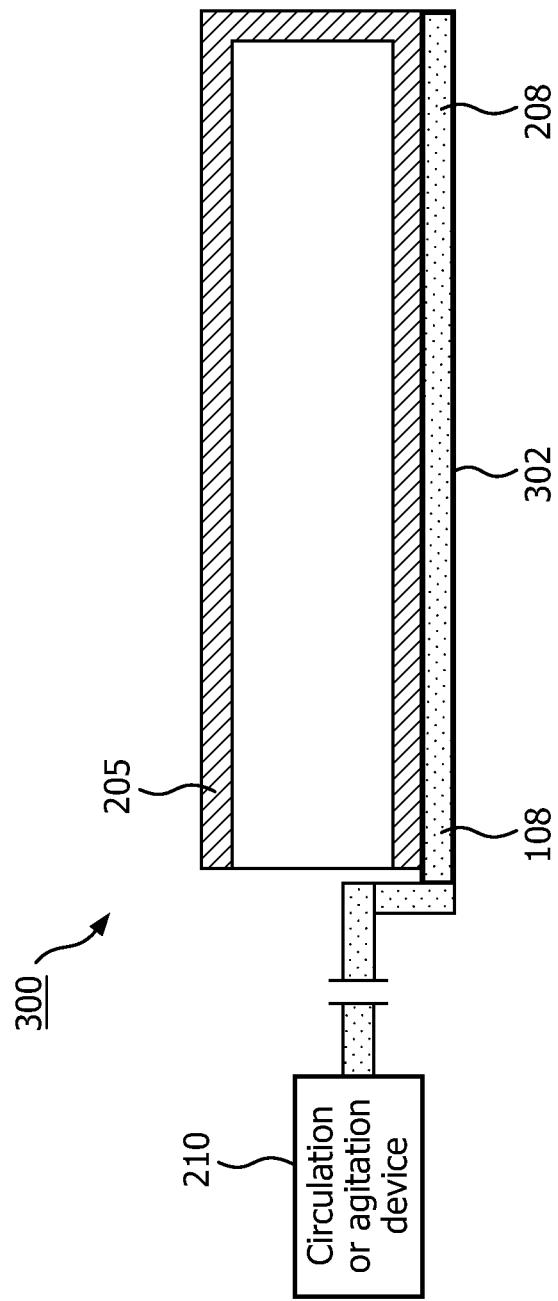
FIG. 3 is a partial cross-sectional view of a medical device having a longitudinal tube containing nanomaterials in suspension in accordance with another embodiment.

Referring to FIG. 3, another medical device 300 is shown in accordance with another illustrative embodiment. Device 300 includes a tube or tubes 302 that run the length or a portion of the length of the medical device 300. The tube or tubes 302 may also wrap around the device (e.g., in a coil, spiral, or other configuration). The tubes 302 carry the nanomaterial suspension 208.

The nanomaterial suspension 208 may be circulated to prevent settling of the nanomaterials 108 using a circulation/agitation device 210. The circulation/agitation device 210 may include one or more of an external pump, a vibration device, an electromagnetic stirring device which mixes by mixing ferromagnetic particles, etc. It should be understood that the circulation/agitation device 210 may be located at or on the device 300 or may be located externally to a patient during a procedure.

Figure 4:
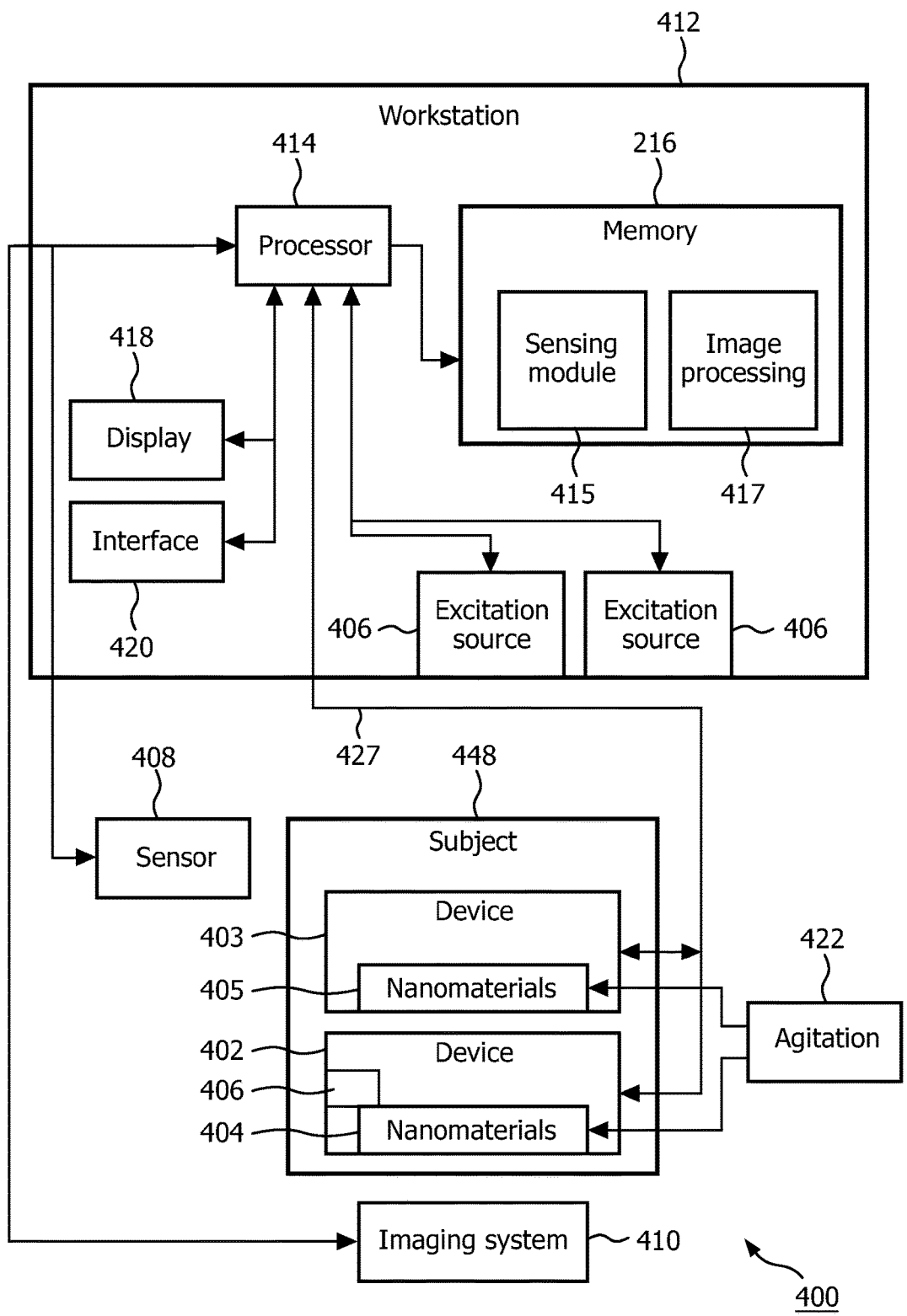
FIG. 4 is a block/flow diagram showing a system for imaging medical devices in accordance with one illustrative embodiment.

Referring to FIG. 4, a system 400 for performing a medical procedure is illustratively depicted. System 400 may include a workstation or console 412 from which a procedure is supervised and managed. Workstation 412 preferably includes one or more processors 414 and memory 416 for storing programs and applications. Memory 416 may store a device sensing module 415 configured to interpret electromagnetic and/or acoustic feedback signals from a nanomaterial layer or suspension 404 (405) of a medical device 402 (403). The sensing module 415 is configured to use the signal feedback (and any other feedback) to provide a location or to depict the medical device 402 (or 403) in medical images. The medical device 402 (403) may include, e.g., a catheter, a guide wire, an endoscope, a probe, a robot, an electrode, a filter device, a balloon device, a needle or other medical component, etc. Workstation 412 may include a display 418 for viewing internal images of a subject using an imaging system 410. The imaging device 410 may include imaging modalities such as optical coherence tomography, confocal microscopy, photoacoustics, etc. The imaging system 410 may also include, e.g., a magnetic resonance imaging (MRI) system, a fluoroscopy system, a computed tomography (CT) system, an ultrasound system or other system where excited nanomaterials may be viewed. Display 418 may also permit a user to interact with the workstation 412 and its components and functions. This is further facilitated by an interface 420 which may include a keyboard, mouse, a joystick or any other peripheral or control to permit user interaction with the workstation 412.

Workstation 412 includes one or more energy or excitation sources 406 to provide excitation energy at predetermined wavelengths. Alternately, one or more excitation sources 406 may be incorporated into the device(s) 403 (or 402), so the incident radiation need not be provided from a source external to the body/subject 448. The excitation wavelengths are selected and the nanomaterials tuned to be sensitive to these wavelengths. This may be performed in-situ or in advance of the procedure. The energy sources 406 may provide electromagnetic energy in the form of infrared, x-ray, visible light, etc. The absorption spectra of the nanomaterials are accordingly adjusted to provide a measurable response to the excitation. A sensor unit 408 is employed to detect electromagnetic energy or acoustic energy returning from the nanomaterials 404 (405). This permits the determination of energy emissions which will be used to interpret a shape and/or orientation of the device 402. The signals will be employed as feedback to make adjustments or otherwise perform the medical procedure. The sensor unit 408 may include a photodetector, an ultrasonic sensor (probe) or other sensor device or devices.

If the nanomaterials are in suspension, a circulation or agitation device 422 may be employed to mix or agitate the suspension to prevent settling of the nanomaterials (404, 405). Imaging system 410 may be provided to collect real-time intra-operative imaging data. The imaging data may be displayed on display and sensing module 415 may compute energy emission positions within the real-time images. A digital rendering of the medical device 402 (using feedback from nanomaterials 404) can be displayed to reveal the position of the device 402 against the real-time images. The digital rendering may be generated by an image processing module 417. In one embodiment, the imaging system 410 includes an ultrasonic system, and the emissions from the nanomaterials 404 are acoustic in nature. In this way, both anatomical images and device images can concurrently be displayed.

In another useful embodiment, an interventional application includes the use of two medical devices inside of a subject 448. For example, one device 402 may include a guide catheter, which is placed at one point, and another device 403 may include a needle for performing an ablation or biopsy at fixed/different points along the length of the catheter. The device 402 includes nanomaterials 404, and device 403 includes nanomaterials 405. In this example, nanomaterials 404 and 405 are two different types of nanomaterials with different peak absorption wavelengths. Nanomaterials 404 are employed to image the guide catheter and nanomaterials 405 are employed to image the needle.

During a procedure, the nanomaterials 404 are excited by a first wavelength and nanomaterials 405 are excited by a different wavelength. In this way, nanomaterials 404 are employed to determine a position of the catheter while nanomaterials 405 on the needle are used to accurately position the needle relative to the catheter.

In another illustrative embodiment, an image subtraction method is employed to better infer a position of the device 402 using the incorporated nanomaterials 404. Since the absorption spectra of the nanomaterials 404 are known, a priori, and the absorption spectra of tissue components are also known, two frequencies for which the absorption coefficients are similar to that of the tissues may be selected, while ensuring that the absorption of the nanomaterials 404 at these two frequencies is different. The patient or subject 448 is first exposed at a first frequency, which results in a first response (emission) by the nanomaterials 404, and is recorded in a first image. Then, the patient is exposed to a second frequency, which results in a second, different response (emission) by the nanomaterials 404, and is recorded in a second image. Then, the image processing module 417 subtracts the second image from the first image to yield information uniquely about the nanomaterials 404 and therefore the position of the medical device 402.

This method can be utilized with any and all of the previous embodiments described to infer locations of devices 402, 403, etc. (e.g., catheters, needles, etc.). For imaging of nanomaterials 404, 405, the incident wavelengths of the electromagnetic radiation are dependent on the nanomaterial and their geometry. For example, gold nanorods with mean aspect ratios of 5.9 and 3.7 exhibit peak optical absorptions at 1000 and 785 nm, respectively. Imaging device 410 provides contrast from the nanomaterials 404, 405 that can be displayed.

Figure 5:
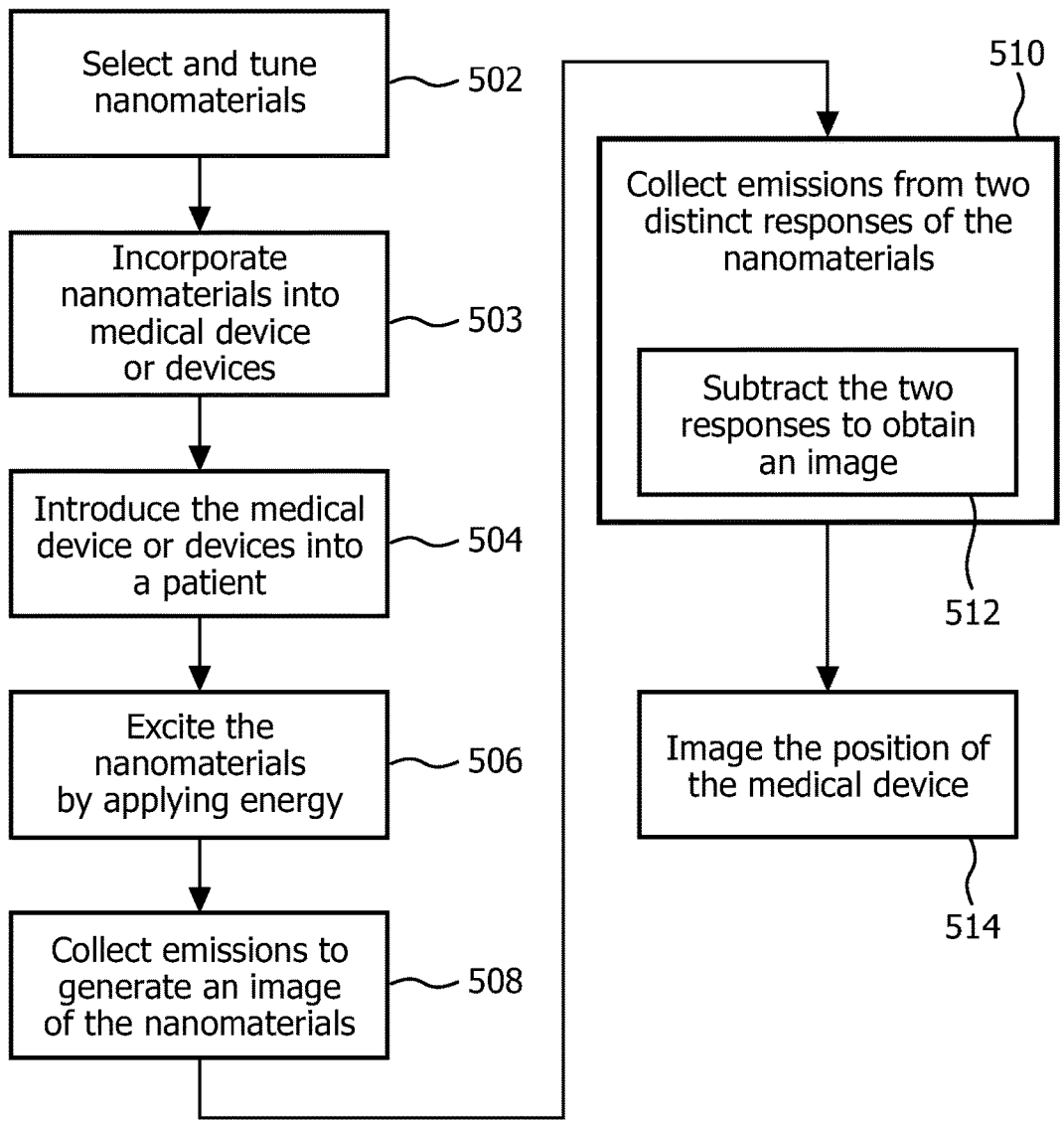
FIG. 5 is a block/flow diagram showing a method for locating and imaging medical devices in accordance with another illustrative embodiment.

Referring to FIG. 5, a method for imaging nanomaterials in accordance with one illustrative embodiment is shown. In block 502, a composition of nanomaterials is selected to be responsive to predetermined wavelengths (or frequencies) of electromagnetic radiation and tuned. The tuning may include material type (e.g., nanospheres, nanotubes CNTs, etc.), material selection (e.g., gold, graphite, etc.), geometry selection (e.g., sixe and shape), dopant concentration, etc. as described herein. In block 503, the composition of nanomaterials is incorporated into one or more medical devices or instruments. The nanomaterials may include materials with same absorption spectra or may include materials with different absorption spectra. In one embodiment, each of the different nanomaterials may be uniquely associated with different devices or a same device may include nanomaterials responsive to different wavelengths/frequencies. In block 504, the one or more medical devices are introduced into a patient (e.g., a mammal) during a medical procedure.

In block 506, electromagnetic frequencies corresponding to excitation frequencies of the one or more types of nanomaterials are selectively applied to excite the nanomaterials. In block 508, image information is collected from response emissions from the nanomaterials. The emissions are responsive to at the least one electromagnetic frequency of excitation. The image information may be employed for locating one or more of the medical devices in anatomical/medical images of the patient.

In block 510, in another embodiment, image information for multiple electromagnetic frequencies of excitation may be obtained for a device or devices. In this example, the device includes nanomaterials that have two distinct excitation frequencies. It is preferable that a second frequency response due to the nanomaterials is recognizably different as compared to a first frequency, and that these responses are different from surrounding regions. For example, the first, second, etc. responses should be different from the response of surrounding tissues and that the tissue response is substantially the same for all the excitation the frequencies.

In block 512, the first and second images are subtracted from one another to obtain image information unique to the nanomaterials of the device. This identifies a position of the medical device in the patient. Such information is employed to infer location of, e.g., catheters, needles, etc. The subtraction may include a simple pixel value subtraction although any useful image processing techniques may be employed.

In block 514, the position of the device or devices may be overlaid on other medical images to provide a technician or physician with a useful location tool for identifying device positions and carrying out the procedure. Such procedures may include, e.g., interventional procedures using catheters, scopes, needles, etc., such as, cardiac catheterization, catheter detection, tracking and positioning during ablation procedures, needle visualization for guidance of tissue biopsy procedures, visualization of other instruments in minimally invasive surgery (endoscopes), etc.

Figure 6:
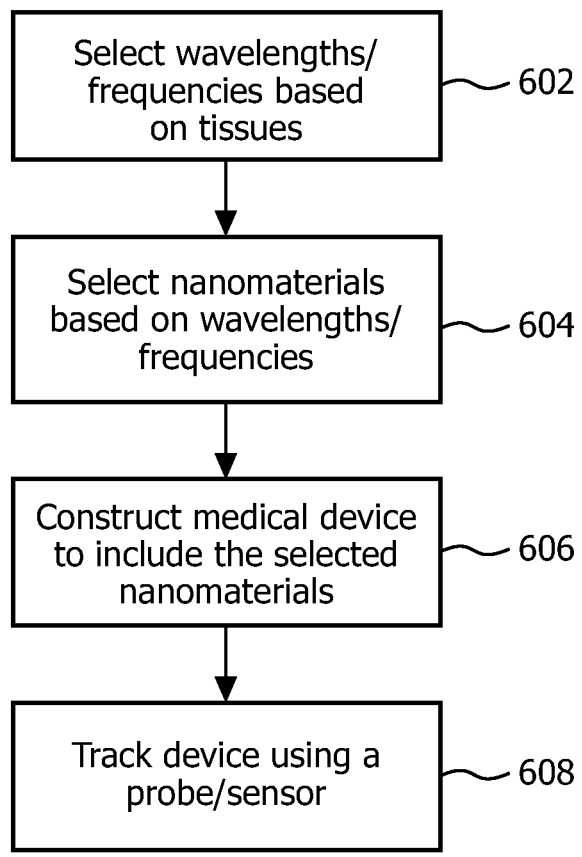
FIG. 6 is a block/flow diagram showing another method for constructing and using a medical device in accordance with an illustrative embodiment.

Referring to FIG. 6, another method for building and using a catheter with desired properties is illustratively depicted in accordance with another particularly useful embodiment. In block 602, wavelengths at which there is minimum absorption by tissues of interest (e.g., human tissue properties at incident wavelengths) are selected. For human tissue, 650 nm-1200 nm is desirable (this includes the near infrared (IR) window of 700-900 nm where light has its maximum depth of penetration in tissue). Other wavelengths may be chosen if the medical device (e.g., catheter or needle) is superficial or outside the body.

In block 604, nanomaterials which have the best absorption at these wavelengths or frequencies are identified. The selection of particle size, shape, etc. is made. These nanomaterials are additionally screened for optimal biocompatibility. The selection of nanomaterials may be made as described above.

In block 606, a medical device is constructed (e.g., the catheter) by coating, layering, etc. the nanomaterials on a surface thereof or forming the device in accordance with one or more of the embodiments disclosed herein. A source of electromagnetic radiation to excite the particles may be provided externally to the device or can be incorporated into the catheter design (so the incident radiation need not be provided from a source external to a body where the device may be employed during a procedure). High power infrared (IR) light emitting diodes (LEDs) may be employed to provide the excitation.

In block 608, photoacoustic signals or other feedback generated by the nanomaterials due to the incident radiation of the device can then be tracked by an ultrasound probe or other sensor on the surface of the body.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for real-time medical device visualization using nanomaterials (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical device configured for internal use within a subject, comprising:

a structure having a length dimension and a surface;

a volume associated with the surface and extending along at least a portion of the length dimension; and nanomaterials incorporated in the volume comprising at least one nanomaterial selected from the group consisting of nanotubes, nanorods, nanospheres, nanocages and quantum dots, said nanomaterials having specific absorption or scattering peaks at defined wavelengths, wherein the nanomaterials are configured to be responsive to at least one excitation signal such that the excitation signal generates an electromagnetic or acoustic signature response from the nanomaterials to enable location of the structure within an interior of the subject, wherein the volume includes a tube forming an annular cavity relative to the surface, the annular cavity including the nanomaterials in suspension, and further comprising an agitation mechanism in communication with the suspension to prevent the nanomaterials from settling.

2. A system for locating a medical device, comprising:

a medical device configured for internal use within a subject, said medical device including nanomaterials incorporated therein, the nanomaterials being selected from the group consisting of nanotubes, nanorods, nanospheres, nanocages and quantum dots, said nanomaterials having specific absorption or scattering peaks at defined wavelengths, wherein the nanomaterials are configured to be responsive to at least one excitation signal to generate an electromagnetic or acoustic signature response;

an excitation source configured to generate the at least one excitation signal to generate the electromagnetic or acoustic signature response from the nanomaterials;

a sensor configured to receive the electromagnetic or acoustic signature response; and an image processing module configured to render the medical device in a medical image using the received electromagnetic or acoustic signature response, further comprising an agitation mechanism in communication with a suspension which includes the nanomaterials, the agitation mechanism to prevent the nanomaterials from settling.

3. A method for locating a medical device, comprising:
providing a medical device configured for internal use within a subject, said medical device having nanomaterials incorporated therein, the nanomaterials selected from the group consisting of nanotubes, nanorods, nanospheres, nanocages and quantum dots, said nanomaterials having specific absorption or scattering peaks at defined wavelengths, wherein the nanomaterials are configured to be responsive to at least one excitation signal such that the excitation signal generates an electromagnetic or acoustic signature response from the nanomaterials;
exciting the nanomaterials using the at least one excitation signal to generate the electromagnetic or acoustic signature response from the nanomaterials;
sensing the electromagnetic or acoustic signature response from the nanomaterials; and
processing the sensed electromagnetic or acoustic signature response from the nanomaterials to locate the medical device in relation to a medical image,
further comprising agitating nanomaterials incorporated in the medical device as a suspension including the nanomaterials to prevent the nanomaterials from settling.

4. A method for generating an image of a medical device configured for internal use within a subject, comprising:
exciting nanomaterials included in a medical device using a first electromagnetic frequency of excitation for the nanomaterials to obtain a first imagable response, the first imagable response being detectable over surrounding materials;
exciting the nanomaterials included in the medical device using a second electromagnetic frequency of excitation for the nanomaterials to obtain a second imagable response which includes a realizable difference from the first imagable response, the second imagable response being detectable over the surrounding materials;
subtracting the first imagable response from the second imagable response to provide an image of the medical device relative to a subject.

5. The method as recited in claim 4, wherein the medical device has nanomaterials incorporated by at least one of a solid layer formed on the medical device; in suspension in an annular cavity formed relative to a device wall of the medical device; or in suspension in a tube formed longitudinally along a device wall of the medical device.

6. The method as recited in claim 4, further comprising agitating nanomaterials incorporated in the medical device as a suspension including the nanomaterials to prevent the nanomaterials from settling.

7. The method as recited in claim 4, further comprising digitally generating an image of the medical device in a medical image.

8. A medical device configured for internal use within a subject, comprising:
a structure having a length dimension and a surface;
a volume associated with the surface and extending along at least a portion of the length dimension;
nanomaterials included in the volume in suspension, the nanomaterials configured to be responsive to at least one excitation signal such that the excitation signal generates a response from the nanomaterials to enable location of the structure within an interior of the subject; and
an agitation mechanism in communication with the suspension to prevent the nanomaterials from settling.

9. A system for locating a medical device, comprising,
a medical device configured for internal use within a subject, said medical device including nanomaterials in suspension incorporated therein, the nanomaterials being configured to be responsive to at least one excitation signal;
an agitation mechanism in communication with the suspension to prevent the nanomaterials from settling;
an excitation source configured to generate the at least one excitation signal to generate response emissions from the nanomaterials;
a sensor configured to receive the response emissions; and
an image processing module configured to render the medical device in a medical image using the response emissions.

10. A method for locating a medical device, comprising:
providing a medical device configured for internal use within a subject, said medical device having nanomaterials in suspension incorporated therein, the nanomaterials being configured to be responsive to at least one excitation signal;
agitating the nanomaterials to prevent the nanomaterials from settling;
exciting the nanomaterials using the at least one excitation signal to generate response emissions from the nanomaterials;
sensing the response emissions; and
processing the response emissions to locate the medical device in relation to a medical image.

* * * * *